(12) United States Patent
Dhuin et al.

(10) Patent No.: US 8,853,275 B2
(45) Date of Patent: Oct. 7, 2014

(54) CONCURRENT THERAPY REGIME/REGIMEN FOR THE TREATMENT OF ACNE RELATED DISEASES

(75) Inventors: Jean-Charles Dhuin, Nice (FR); Nabil Kerrouche, Le Rouret (FR); Stéphanie Arsonnaud, Le Rouret (FR); Pascale Soto, Antibes (FR)

(73) Assignee: Galderma Research & Development, Biot (FR)

( * ) Notice: Subject to any disclaimer, the term of this patent is extended or adjusted under 35 U.S.C. 154(b) by 546 days.

(21) Appl. No.: 12/992,425

(22) PCT Filed: May 18, 2009

(86) PCT No.: PCT/EP2009/056015
§ 371 (c)(1),
(2), (4) Date: Mar. 11, 2011

(87) PCT Pub. No.: WO2009/138516
PCT Pub. Date: Nov. 19, 2009

(65) Prior Publication Data
US 2011/0183943 A1    Jul. 28, 2011

Related U.S. Application Data

(60) Provisional application No. 61/053,942, filed on May 16, 2008.

(51) Int. Cl.
| | | |
|---|---|---|
| *A01N 37/10* | (2006.01) | |
| *A61K 31/19* | (2006.01) | |
| *A01N 31/00* | (2006.01) | |
| *A61K 31/075* | (2006.01) | |
| *A01N 27/00* | (2006.01) | |
| *A61K 31/015* | (2006.01) | |
| *C07C 69/76* | (2006.01) | |
| *C07C 63/36* | (2006.01) | |
| *C07C 233/00* | (2006.01) | |
| *C07C 235/00* | (2006.01) | |
| *C07C 237/00* | (2006.01) | |
| *C07C 239/00* | (2006.01) | |
| *A61K 31/327* | (2006.01) | |
| *A61K 45/06* | (2006.01) | |
| *A61K 31/192* | (2006.01) | |
| *A61K 31/65* | (2006.01) | |
| *A61K 31/203* | (2006.01) | |
| *A61K 31/7056* | (2006.01) | |

(52) U.S. Cl.
CPC ............. *A61K 31/192* (2013.01); *A61K 31/327* (2013.01); *A61K 45/06* (2013.01); *A61K 31/65* (2013.01); *A61K 31/203* (2013.01); *A61K 31/7056* (2013.01)

USPC ............. 514/569; 514/714; 514/765; 560/60; 562/490; 564/180

(58) Field of Classification Search
USPC ............. 514/569, 714, 765; 560/60; 562/490; 564/180
See application file for complete search history.

(56) References Cited

FOREIGN PATENT DOCUMENTS

| WO | WO 02080932 A1 | * | 10/2002 |
|---|---|---|---|
| WO | WO 2004/064803 A1 | | 8/2004 |
| WO | WO 2006045640 A1 | * | 5/2006 |
| WO | WO 2007/002831 A2 | | 1/2007 |
| WO | WO 2008/006888 A1 | | 1/2008 |

OTHER PUBLICATIONS

Hurwitz et al., "The combined effect of vitamin A and Benzoyl peroxide in the treatment of acne", Cutis, Excerpta Medica, 1976, pp. 586-589, vol. 17, No. 3.
Bikowski "Clinical experience results with clindamycin 1% benzoyl peroxide 5% gel (DUAC®) as monotherapy and in combination", Journal of Drugs in Dermatology, 2005, pp. 164-171, vol. 4, No. 2.
Gollnick et al., "Management of acne—A report from a global alliance to improve outcomes in acne", J of the American Academy of Dermatology, 2003, pp. S1-S37, vol. 49, No. 1.
Thiboutot et al., "Treatment considerations for inflammatory acne: clinical evidence for adapalene 0.1% in combination therapies", Journal of Drugs in Dermatology, 2009, pp. 785-794, vol. 5, No. 8.
Thiboutot et al., "Combination therapy with adapalene gel 0.1% and doxycycline for severe acne vulgaris: a multicenter, investigator-blind, randomized, controlled study", Skinmed, 2005, pp. 138-146, vol. 4, No. 4.
International Search Report corresponding to PCT/EP 2009/056015, Aug. 6, 2009.
Thiboutot et al., "Adapalene-benzoyl peroxide, a fixed-dose combination for the treatment of acne vulgaris: Results of a multicenter, randomized double-blind, controlled study", J. Am. Acad. Dermatol., 2007, pp. 791-799, vol. 57, No. 5.
Thevarajah et al., "Trends in prescription of acne medication in the US: Shift from antibiotic to non-antibiotic treatment", J. Dermatological Treatment, 2005, pp. 224-228, vol. 15, No. 4.
Eady et al., "Antibiotic resistant propionibacteria in acne: need for policies to modify antibiotic usage," British Medical Journal, 1993, pp. 555-556, vol. 306, No. 6877.

* cited by examiner

*Primary Examiner* — Sarah Pihonak
(74) *Attorney, Agent, or Firm* — Dentons US LLP

(57) ABSTRACT

A novel therapy regime/regimen for the treatment of acne related diseases includes administering a topical fixed-dose combination of a retinoid and an anti-bacterial agent, such as BPO, to a course of oral antibiotic therapy.

7 Claims, 2 Drawing Sheets

CONCURRENT THERAPY REGIME/REGIMEN FOR THE TREATMENT OF ACNE RELATED DISEASES

CROSS-REFERENCE TO EARLIER APPLICATIONS

Figure 1:
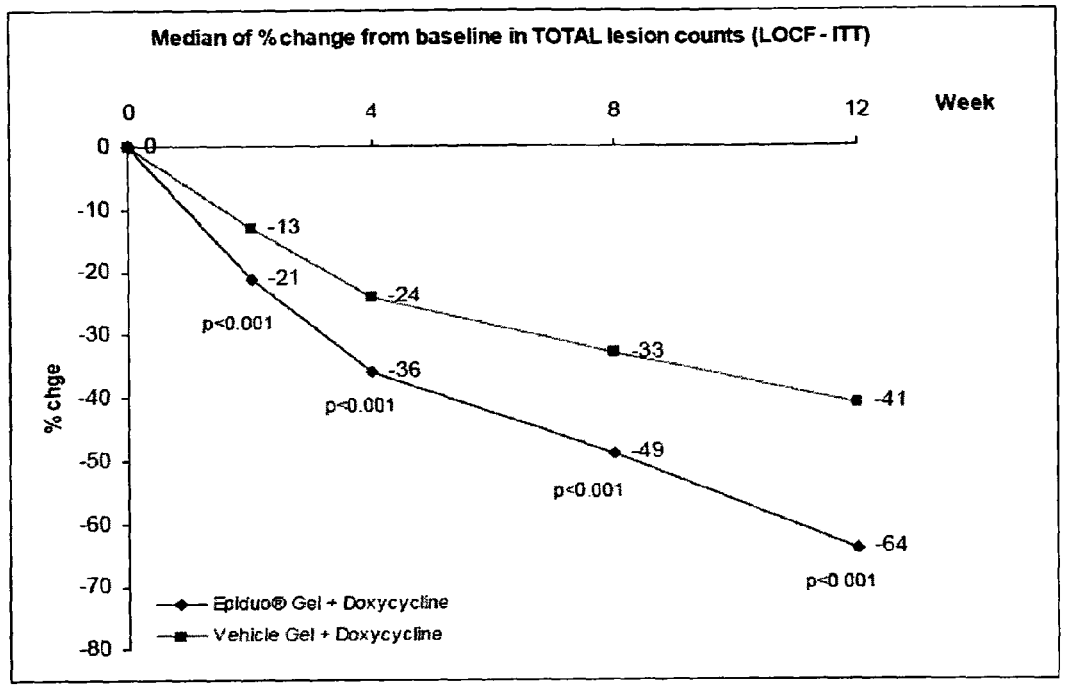

This application is the U.S. National Stage of PCT/EP 2009/056015, filed May 18, 2009 and designating the United States (published in the English language on Nov. 19, 2009, as WO 2009/138516 A1), which claims benefit of U.S. Provisional Application No. 61/053,942, filed May 16, 2008, each earlier application hereby expressly incorporated by reference in its entirety and each assigned to the assignee hereof.

FIELD OF THE INVENTION

This invention relates to a new therapy regimen for treating acne related diseases, particularly acne vulgaris. The regimen includes a topical treatment with a fixed-dose combination of a retinoid, such as Adapalene, and an anti-bacterial agent, such as benzoyl peroxide (BPO), and an oral antibiotic drug.

BACKGROUND OF THE INVENTION

The burden of acne is significant. More than 50 million Americans experience some form of acne. Acne vulgaris is a common skin disorder that makes up 20% of the visits to dermatologists, and affects approximately 80% of young adults and adolescents. Management of acne is challenging, especially considering the chronicity of the disease and the variability in response to treatments. Acne management can be complex, because the disease is multifactorial, involving various etiological features, including follicular hyperkeratinisation, increased sebum production, *P. acnes* proliferation, and inflammation.

Oral isotretinoin (13-cis-retinoic acid) is currently the only medication that affects all of the major acne pathogenic factors. However, this drug has been associated with multiple serious side effects, the most serious of which is teratogenicity. Therefore, for inflammatory acne, except for the most severe or aggressive cases of the disease, alternative treatments, such as the combination of an oral antibiotic and a topical treatment, should be the preferred option.

The bulk of the current evidence for topical retinoid-oral antibiotic combination therapy in inflammatory acne is with Adapalene 0.1%. One study in particular demonstrated that the combination of 100 mg of Doxycycline with Adapalene gel 0.1% led to a greater and faster improvement compared to the oral antibiotic alone. See "Combination therapy with adapalene gel 0.1% and doxycycline for severe acne vulgaris: a multicenter, investigator-blind, randomized, controlled study", Skinmed. 2005, May-June; 4(3):138-46.

The recent Consensus Recommendations for the Management of Acne (JAAD sup 2003; 49:1) states that effective acne treatment should target as many of its pathogenic factors as possible.

The recommendations also state that a topical retinoid should be used in the initial treatment of almost all new patients with acne, because they are the most effective anti-comedonal agents currently available. Retinoids help disrupt acne pathogenesis by preventing the development of new microcomedones, and some possess both direct and indirect anti-inflammatory activity.

The management of acne often requires combination therapy and a long-term therapeutic strategy. See, for example, Thiboutot D. New treatments and therapeutic strategies for acne, Arch Family Med 2000; 9: 179-187; Gollnick H., et al. Management of Acne, a report from a Global Alliance to Improve Outcomes in Acne, J. Am. Acad. Dermatol., 2003; 49(1 suppl):S1-537).

Recently, a unique fixed-dose combination of adapalene and benzoyl peroxide in a form of gel (Adapalene BPO Gel) has been granted with Marketing Authorization in Europe and US under the trade name of Epiduo® (Galderma). Adapalene BPO Gel is a unique antibiotic-free combination of Adapalene 0.1%, a well-tolerated and efficacious topical retinoid, and BPO 2.5%, a well established antimicrobial agent. The complementary modes of action, efficacy and safety profiles of these two agents make Adapalene BPO Gel the most appropriate choice for once-daily treatment for all types of acne except for the most severe cases. Adapalene (6-[3-(1-adamantyl)-4-methoxyphenyl]-2-naphtoïc acid) possesses anti-comedogenic, comedolytic, and anti-inflammatory properties whereas BPO, the most potent bactericidal agent, is more effective than other topical antibiotics against *P. acnes*. See "Adapalene-Benzoyl Peroxide, A Unique Fixed-Dose Combination Gel For Acne treatment: A Randomized, Double-Blind, Controlled Trial In 1668 Patients" (http://www.galdermanordic.com/sverige/pdf/FP0039.pdf). Because neither retinoids nor BPO creates selective pressure for resistance, this combination may be expected to decrease the incidence of epidermal bacterial resistance relative to antibiotics. Furthermore, unlike tretinoin, Adapalene is stable in the presence of light when combined with BPO. See "Adapalene-Benzoyl Peroxide Combination Effective and Safe for Acne", CME Released: Nov. 9, 2007; Valid for credit through Nov. 9, 2008.

Efficacy and safety of Adapalene BPO Gel has been established in a large clinical program. Adapalene BPO Gel combination provides significantly greater efficacy for the treatment of moderate acne vulgaris and a quicker onset of action relative to respective monotherapies, with a comparable safety and tolerability profile relative to Adapalene.

Moreover, acne vulgaris is a multi-factorial disease characterized by:

Overproduction of sebum,

Microcomedone and comedone formation caused by hyperkeratosis of the follicular epithelium and retention keratosis, Proliferation of microbes, particularly *P. acnes* in the sebum, and Inflammation resulting from the rupture of comedones.

If not appropriately treated, acne may cause serious physical and emotional scarring and can significantly impact the quality of life of those affected by the disease.

The ideal treatment regimen for the disease would take into consideration the underlying pathology for each of these factors. Unfortunately, except for oral isotretinoin, no single product exists that addresses all of the factors. As a result, there is still an unmet medical need to improve the treatment of severe inflammatory acne vulgaris that addresses most of acne causing factors.

It is therefore the objective of this invention to provide a novel therapy regimen for the treatment of acne related diseases that avoids the adverse effects of oral isotretinoin and addresses most of acne causing factors.

SUMMARY OF THE INVENTION

This invention provides a novel therapy regimen for the treatment of acne related diseases. The novel therapy regimen of this invention adds a topical fixed-dose combination of a retinoid and an anti-bacterial agent, such as BPO, to a course of oral antibiotic therapy. The regime provides unexpected synergistic results for the treatment of acne related diseases. Further, the regimen prevents future lesion development after oral therapy has been discontinued; therefore, avoiding potential bacterial resistance associated with prolonged oral antibiotic therapy.

Accordingly, this invention relates to a therapy regimen for inhibiting or treating acne related diseases. The regimen includes topically applying to an individual subject in need a therapeutically effective amount of a fixed-dose combination having at least a retinoid and at least a topical antibacterial agent; administering a therapeutically effective amount of an oral antibiotic product with the fixed-dose combination for a predetermined period of time; and optionally continuing the fixed dose combination for another period of time as needed. In a preferred embodiment, A regimen wherein acne related diseases is acne vulgaris; more preferably moderate to severe acne.

In one embodiment, the retinoid is preferably Adapalene. In an another embodiment the topical antibacterial agent is preferably benzoyl peroxide.

In a preferred embodiment, the fixed-dose combination comprises Adapalene and benzoyl peroxide admixed in a pharmaceutically acceptable carrier.

According to one embodiment, the fixed-dose combination is applied once a day. Preferably, the fixed-dose combination is applied in the evening and the oral antibiotic product is administered in the morning.

In a preferred embodiment, the fixed-dose combination of Adapalene and Benzoyl peroxide is in a gel. Preferably, an aqueous gel.

According to a particular embodiment, the oral antibiotic product is selected from the group consisting of lymecycline, clindamycin, doxycycline, avosulfone; macrolides, erythromycin, ampicillin, aminoglycosisdiques, kanamycin, synergistines, and pristinamycin. Preferentially, the oral antibiotic product is selected from the group consisting of lymecycline, clindamycin, and doxycycline.

Another embodiment of the inventions concerns a therapy regimen kit for inhibiting or treating acne related diseases comprising (a) a package containing a composition comprising at least one retinoid and at least one topical antibacterial agent; (b) a package containing an oral antibiotic product; and (c) an instruction to facilitate patient compliance with the therapy regimen.

Another embodiment of the invention regards, the use of a fixed-dose combination of a retinoid and at least an antibacterial agent for the preparation of a composition intended for inhibiting or treating acne-related disease comprising: (a) topically applying to an individual subject in need a therapeutically effective amount of a fixed-dose combination comprising at least an retinoid and at least a topical antibacterial agent; (b) administering a therapeutically effective amount of oral antibiotic product with the fixed-dose combination for a predetermined period of time; and (c) optionally continuing the fixed dose combination for another period of time as needed. In a preferred embodiment, the retinoid is adapalene. In another also preferred embodiment, the antibacterial agent is the benzoyl peroxide.

Other features and advantages of this invention will be apparent from the detailed description of this invention and from the claims.

DETAILED DESCRIPTION OF THE INVENTION

We believe that one skilled in the art can, based upon the description herein, use the present invention to its fullest extent. The following specific embodiments are to be construed as merely illustrative, and do not serve to limit the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Definitions

As used herein in the specification and in the claims section below, the term "inhibit" and its derivatives refer to suppress or restrain from of occurrence or recurrence of the condition or disease to be treated, as such the regimen of this invention will reduce the likelihood for recurrence of the condition or disease to be treated.

As used herein, the term "treating" or "treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

The term "topical" and its derivatives as used herein refers to directly laying on or spreading on the skin in need of the treatment, e.g., by use of the hands or an applicator.

The term "subject" as used herein refers to mammalian animals, preferably human.

The term "therapeutically effective amount" of a therapeutic agent as used herein refers to an amount of each active component of the pharmaceutical formulation that is sufficient to show a meaningful patient benefit, i.e., to cause a decrease in, amelioration of, or prevention of the symptoms of the condition being treated. Effective amounts of the pharmaceutical formulation will vary according to factors such as the degree of susceptibility of the individual, the age, gender, and weight of the individual and idiosyncratic responses of the individual.

As used herein, the term "fixed-dose" of the therapeutic agents refers to a combination dose that is administered to a human patient without regard for the weight (WT) or body surface area (BSA) of the patient. The fixed dose is therefore not provided as a mg/kg dose or a mg/m2 dose, but rather as an absolute amount of the therapeutic agent.

As used herein, "oral" means administering a composition that is intended to be ingested. Examples of oral forms include, but are not limited to, tablets, pills, capsules, powders, granules, solutions or suspensions, and drops. Such forms may be swallowed whole or may be in chewable form. Oral forms do not include compositions intended to be topically administered to the skin.

As used herein, "pharmaceutically-acceptable" means active agents, inert ingredients, or composition that are suitable for topical or oral administration without undue toxicity, incompatibility, instability, irritation, allergic response, and the like, commensurate with a reasonable benefit/risk ratio.

Fixed-Dose Combination

The Fixed-dose combination, according to this invention, comprises at least one retinoid and at least one topical antibacterial agent. The retinoid and the topical antibacterial agent are applied with a single topical composition comprising both the retinoid and the topical antibacterial agent.

The term "fixed dose combination" should be understood as meaning a combination whose active principles are combined at fixed doses in the same vehicle/medium (single formula) that delivers them together to the point of application. Preferably, the pharmaceutical composition in the form of a fixed combination is a gel; in this case, the two active principles are dispersed and intimately mixed, during the manufacture, in the same vehicle, which delivers them together during the application of the gel.

As used herein, the term "retinoid" refers to a class of compounds consisting of four isoprenoid units joined in a head-to-tail manner. Retinoids may be formally derived from a monocyclic parent compound containing five carbon-carbon double bonds and a functional group at the terminus of the acyclic portion. Retinoids suitable for this invention are those that are effective for treating acne. Examples of retinoids useful in this invention include tretinoin, isotretinoin, tazarotene, adapalene, benzoic acid-terminated retinoids and their heterocyclic analogs, the pharmaceutically acceptable salts and esters thereof and the like and mixtures thereof.

The term "antibacterial agent" as used herein refers to any substance of natural, semi-synthetic or synthetic origin, including all known antibiotics, that kills or inhibits the growth of one or more bacteria, but causes little or no host damage.

As used herein, the term "topical antibacterial agent" refers to a class of antibacterial agents that are suitable for topical application. Examples of such topical antibacterial agents for use herein include, but are not limited to, benzoyl peroxide, and topical antibiotics such as fluoroquinolone, β-lactam, tetracycline, macrolide, aminoglycoside, glycopeptide, linezolid, amikacin, gentamicin, tobramycin, imipenem, meropenem, cefotetan, cefoxitin, cefuroxime, cefoperazone, cefotaxime, ceftazidime, ceftozoxime, ceftriaxone, cefepime, azithromycin, ampicillin, mezlocillin, piperacillin, ticarcillin, ciprofloxacin, levofloxacin, alatrofloxacin, gatifloxacin, minocycline, chloramphenicol, clindamycin, vancomycin, cefazolin, penicillin G, nafcillin, ofloxacin, and oxacillin.

In a preferred embodiment, the topical composition comprises a therapeutically effective amount of (i) Adapalene, (ii) benzoylperoxide, and (iii) a pharmaceutically-acceptable topical carrier. The topical composition of this invention may be prepared using methodology that is well known by an artisan of ordinary skill.

Optimal dosages to be administered may be readily determined by those skilled in the art, and will vary with the particular extract(s) used, the mode of administration, the strength of the preparation, and the advancement of the disease/condition being treated. In addition, factors associated with the particular individual being treated, including individual's age, weight, diet and time of administration, will result in the need to adjust dosages.

Advantageously, the fixed-dose composition comprises between 0.0001 and 20% by weight of BPO and between 0.0001 and 20% by weight of adapalene relative to the total weight of the composition; preferentially respectively between 0.025 and 10% by weight of BPO and between 0.01% and 2% by weight of adapalene relative to the total weight of the composition.

In a preferred embodiment, BPO is used with concentrations between 2% and 10% by weight and preferentially between 2.5% and 5% by weight relative to the total weight of the composition. Adapalene is used in this kind of composition in concentration between 0.01% and 1% by weight and preferentially between 0.01% and 0.5%, most preferred 0.1% to 0.3% by weight relative to the total weight of the composition.

The compositions may be made into a wide variety of articles that include but are not limited to ointments, lotions, creams, gels, and pastes.

Ointments, as is well known in the art of pharmaceutical formulation, are semi-solid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable-bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Lotions, are preparations to be applied to the skin surface without friction, and are typically semi-liquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Creams, as also well known in the art, are viscous liquids or semi-solid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

As will be readily be understood by those skilled in the field of pharmaceutical formulation, gels are semi-solid, suspension-type systems. Gel forming agent for use herein can be any gelling agent typically used in the pharmaceutical art for topical semi solid dosage forms. Single-phase gels contain organic macromolecules distributed substantially uniformly throughout the carrier liquid, which is typically aqueous, but also can contain an alcohol and optionally an oil. In order to prepare a uniform gel, dispersing agents such as alcohol or glycerin can be added, or the gelling agent can be dispersed by titration, mechanical mixing or stirring, or combinations thereof. The amount of gelling agents varies widely and will ordinarily range from about 0.1% to about 2.0% by weight, based on the total weight of the composition. The gel forming agent also works by the principle of copolymerization. Under alkaline pH, carbomer in presence of water undergoes cross linking and forms a gel like structure. The degree of polymerization is dependent upon the pH. At a threshold pH, the viscosities achieved by the polymer grade is the maximum.

In a specific embodiment, the said fixed-dose combination composition comprises Adapalene and Benzoyl peroxide in a form of gel such as described in WO03/055472 and incorporated herein by reference and preferably is in a form an aqueous gel.

Pastes are semi-solid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Antibiotic Product:

Antibiotic product suitable for the invention includes any antibiotic known by skilled in the art and appropriate to be carried out in the context of the invention. Antibiotic product for the invention is preferably administrable orally.

As used herein, the term "oral antibiotic product" refers to a class of antibiotic agents that are suitable for oral administration. Examples of such antibiotic agents for use herein include, but are not limited to, tetracyclines, penicillins, nitroimidazoles, cephalosporins of each generations; aminoglycosides, carbamens, chloramphenicol, fluoroquinolones, lincosamides, macrolides/ketolides, Oxazolidinones, sulfonamides, azoles antifungals, and other antifungals and their pharmaceutically acceptable salts.

According to a particular embodiment of the invention, the antibiotic product is selected from the group consisting of cyclines such as lymecycline, clindamycin, doxycycline; Sulfones such as avosulfone; Macrolides such as erythromycin; penicillin/B-lactam antibiotics such as ampicillin; Aminoglycosisdiques such as kanamycin; and synergistines such as pristinamycin. In a preferred embodiment, the antibiotic product is selected from the group consisting of lymecycline, clindamycin, and doxycycline. Doxycycline is preferably administered as its hyclate salt or as a hydrate, preferably monohydrate.

The Kit:

In order to facilitate compliance with the present regimen, the components thereof may be provided as a kit. The kit may include, for example, a package containing a composition comprising at least one retinoid and at least one topical antibacterial agent; (b) a package containing an oral antibiotic product; and (c) an instruction to facilitate patient compliance with the therapy regimen in accordance with the present disclosure. The instruction for accomplishing the present regiment may be printed on the outer container of the kit or provided as a separate sheet inserted therein. It is also contemplated that the kit may optionally include a cleanser (such as, for example, a shower gel) for use in cleaning the afflicted area prior to application of the benzoyl peroxide containing composition.

The Treatment:

The therapy regimen of this invention is directed toward the treatment of acne related diseases.

As used herein, the term "acne related disease" is used to describe the conditions of the skin characterized by inflammatory follicular, papular and pustular eruptions involving the sebaceous apparatus. Although there are numerous forms of acne, the most common form is known as acne simplex or acne vulgaris which is characterized by eruptions of the face, upper back and chest and is primarily comprised of comedones, cysts, papules and pustules on an inflammatory base. The condition occurs primarily during puberty and adolescence due to an overactive sebaceous apparatus which is believed to be affected by hormonal activity.

In a preferred embodiment, the acne related disease is acne vulgaris. In a more preferred embodiment, acne is moderate to severe acne, preferably severe inflammatory acne vulgaris.

According to one embodiment of the invention, the therapy regimen may be administered once a day between from 12 hours to 36 hours intervals. The therapy regimen may also be administered every other day, that is, the average period of time between doses is about 48 hours, such as between 36 and 60 hours. An occasional missed dose during the course of treatment does not take the treatment regimen out of the scope of the invention.

Preferably, the fixed-dose combination composition comprising Adapalene and Benzoyl peroxide is applied in the evening and antibiotic product is administered in the morning. In a preferred embodiment, the fixed-dose combination composition comprising Adapalene and Benzoyl peroxide is applied topically and the antibiotic product is administered orally.

The duration of the therapy regimen can be easily determined by a personal skilled in the art according to the labels or recommendations of the manufacturers of the therapeutic compositions or products of this invention, and according to the conditions and other individual considerations of the subjects being treated.

According to this invention, the topical application of the fixed dose combination composition may continue after the termination of the oral antibiotic product. The duration of such period may also been easily determined according to the labels or recommendations of the manufacturers of the therapeutic agents or products, and according to the conditions of the subjects. This enables the subjects to avoid potential bacterial resistance associated with prolonged oral antibiotic therapy.

One skilled in the art will recognize that, both in vivo and in vitro trials using suitable, known and generally accepted cell and/or animal models are predictive of the ability of an extract to treat or prevent a given condition. One skilled in the art will further recognize that human clinical trails including first-in-human, dose ranging and efficacy trials, in healthy individuals and/or those suffering from a given condition or disorder, may be completed according to methods well known in the clinical and medical arts.

Other features and advantages of the present invention will be apparent from the detailed description of the invention and from the claims.

DETAILED DESCRIPTION OF FIGURES

FIG. 1, provides the Efficacy results for total lesion counts (primary criterion) and expressed in Median of % change from baseline in TOTAL lesion counts (LOCF–ITT) from week O to week 12.

Figure 2:
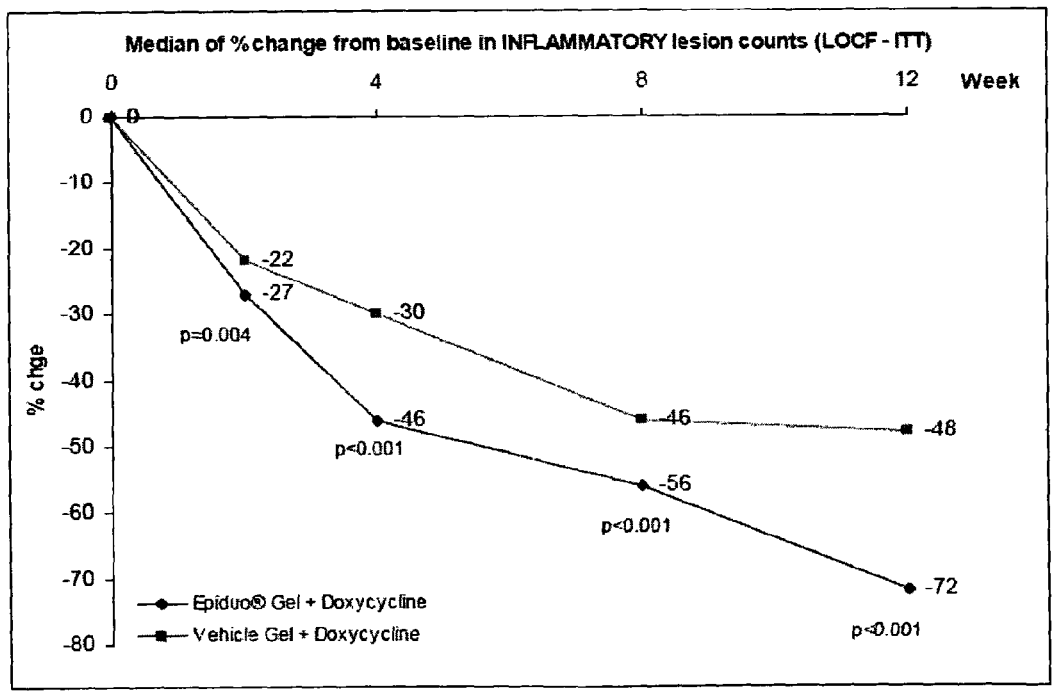

FIG. 2, shows the Efficacy results for inflammatory lesions (secondary criterion) and expressed in Median of % change from baseline in INFLAMMATORY lesion counts (LOCF–ITT) from week O to week 12.

Figure 3:
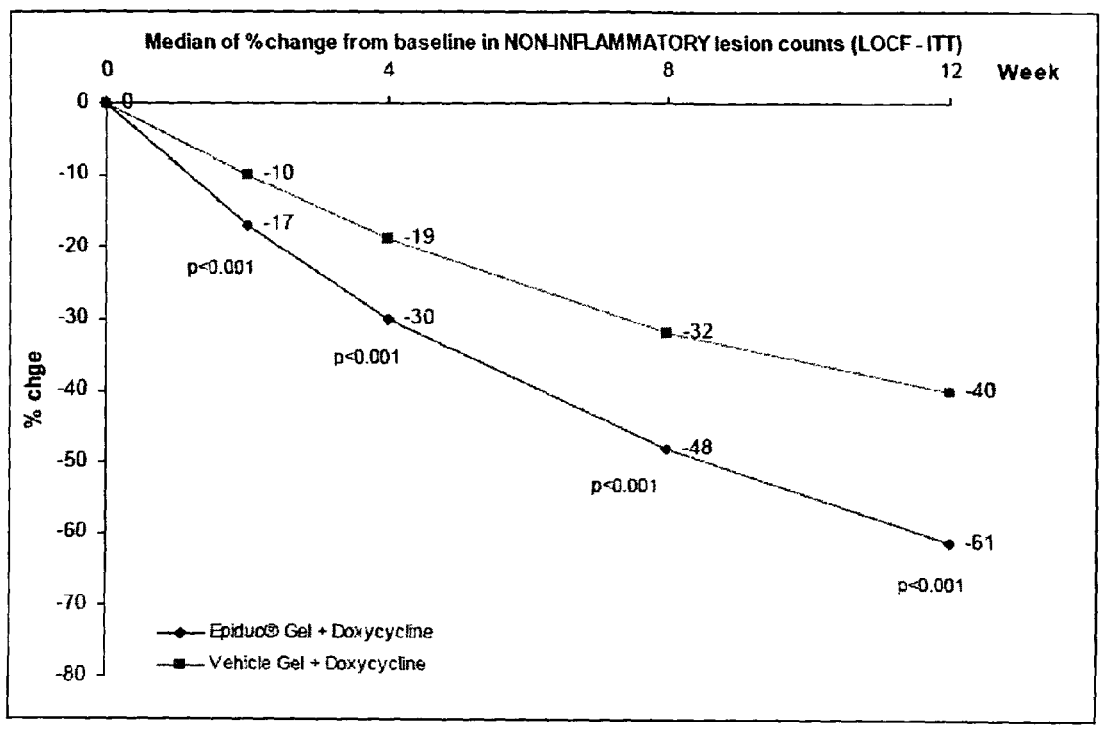

FIG. 3, provides the Efficacy results for non-inflammatory lesions (secondary criterion) and expressed in Median of % change from baseline in NON-INFLAMMATORY lesion counts (LOCF–ITT) from week O to week 12.

Figure 4:
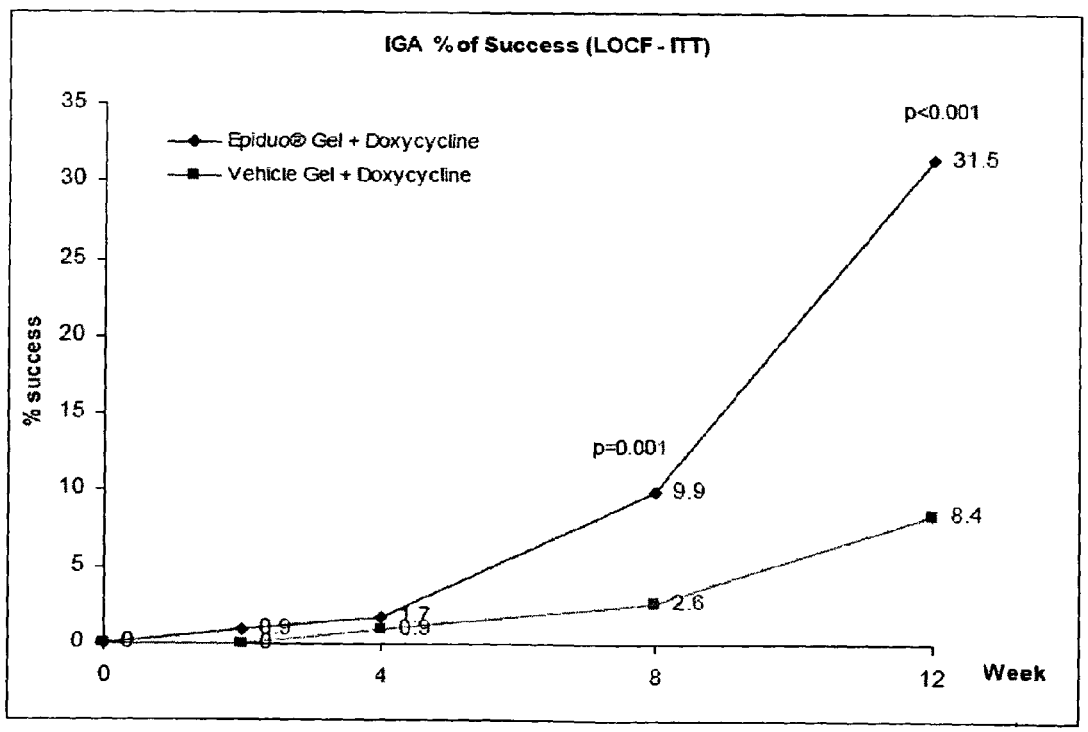

FIG. 4, shows the Efficacy results for Investigator Global Assessment (secondary criterion) and expressed in IGA % of Success (LOCF-ITT)

EXAMPLES

The present invention will be further illustrated below by way of Examples, but the present invention is not limited thereto.

Example 1

Study Protocols for Clinical Test of Treatment of Severe Acne Vulgaris with a Gel Composition Containing Adapalene 0.1%/Benzoyl Peroxide 2.5% Gel Associated with Doxycycline Hyclate 100 mg Tablets This example was the first study evaluating the concomitant use of these treatments. The purpose of this study was to show a superiority in terms of efficacy of Adapalene 0.1%/Benzoyl Peroxide 2.5% Gel (quoted below as Adapalene BPO Gel) associated with Doxycycline Hyclate 100 mg tablets (quoted below as Doxycycline) compared to Adapalene 0.1%/Benzoyl Peroxide 2.5% Vehicle Gel (quoted below as Vehicle Gel) associated with Doxycycline Hyclate 100 mg tablets, in the treatment of severe acne vulgaris.

Study Population

A total of 440 subjects were enrolled (220 in each group) in approximately 30 to 40 sites.

Male or female Subjects of any race, between the age of 12 and 35 years inclusive, with a diagnosis of severe acne vulgaris and meeting specific following inclusion/exclusion criteria.

Inclusion Criteria

1. Male or female Subjects of any race, aged 12 to 35 years inclusive,
2. Subjects with severe facial acne vulgaris (global severity score of 4),
3. Subjects with a minimum of 20 Inflammatory Lesions (papules and pustules) on the face, excluding the nose,
4. Subjects with a minimum of 30 and a maximum of 120 Non-Inflammatory Lesions (open comedones and closed comedones) on the face, excluding the nose,
5. Female Subjects of childbearing potential with a negative urine pregnancy test at the Baseline visit and must practice a highly effective method of contraception during the study: oral/systemic [injectable, patch . . . ] contraception (must have been on a stable dose for 3 months prior to study entry), Intrauterine Device, strict abstinence, condoms, diaphragms, sponge, spermicides or partner had a vasectomy,
6. Females of non-childbearing potential, i.e., premenses, post-menopausal (absence of menstrual bleeding for 2 years), hysterectomy, bilateral tubal ligation, or bilateral ovariectomy, secondary infertility and sterility are not required to have a UPT at the beginning of the study,
7. Subjects have to read and sign the approved the Informed Consent form prior to any participation in the study. Subjects under age of majority may sign an assent form to participate in the study and they must have one parent or guardian read and sign the Informed Consent form prior to any study related procedure (but the parent or guardian is not required to attend the following visits unless requested),
8. For US sites only; subject is apprised of the Health Insurance Portability and Accountability Act (HIPAA): the subject is willing to share personal information and data as verified by signing a written authorization,
9. Subjects willing and capable of cooperating to the extend and degree required by the protocol,
10. If eligible, subjects must be willing to participate to a further 6-month randomized maintenance study assessing maintenance therapy with Adapalene BPO Gel versus its Vehicle Gel (providing his/her acne is enough improved at Week 12 or condition clear at Early Termination visit). Approximately 280 patients only will take part to this maintenance study (RD.03.5PR.29075).

Exclusion Criteria

1. Subjects with more than 2 nodules or cysts on the face,
2. Subjects with acne conglobata, acne fulminans, secondary acne (chloracne, drug-induced acne, etc.),
3. Female Subjects who are pregnant, nursing or planning a pregnancy during the study,
4. Subjects with a wash-out period for topical treatment on the face less than (see table below):
5.

| | |
|---|---|
| Corticosteroids, antibiotics, antibacterials, antiseptics, retinoids, other anti-inflammatory drugs or other acne treatments | 2 weeks |
| Zinc containing drugs | 1 week |
| Phototherapy devices for acne and cosmetic procedures (i.e., facials, peels, comedone extraction) | 1 week |

6. Subjects with a wash-out period for systemic treatment less than (see table below):

| | |
|---|---|
| Corticosteroids, Antibiotics (except plain penicillin) | 4 weeks |
| Oral contraceptives for acne treatment (e.g. Ortho Tri-cyclen ®, Yasmin ®, Alesse ®) | 6 months |
| Other acne treatments (including isotretinoin) | 6 months |
| Ciproterone acetate | 6 months |
| Spironolactone | 3 months |

NOTE:
Oral vitamin A up to the recommended daily dose, 4000-5000 IU, is acceptable 7. Subjects who are treated or are planning to be treated with penicillin,
8. Subjects requiring the use of enzyme inducing drugs such as barbiturates, carbamazepine, phenytoin, and rifampin,
9. Subject who are treated or are planning to be treated with methoxyflurane,
10. Subjects with a condition or who are in a situation which, in the Investigator's opinion, may put the Subject at risk (e.g. history of significant renal disease with impairment of renal function), may confound the study results, or may interfere with the Subject's participation in the study,
11. Subjects who are at risk in terms of precautions, warnings, and contraindications (see package insert and/or investigator brochure),
12. Subjects with known or suspected allergy to one of the investigational products (see package insert and/or investigator brochure),
13. Subjects who have participated in another investigational drug or device research study within 30 days of enrollment,
14. Subjects with a beard or other facial hair that might interfere with study assessments,
15. Subjects who foresee intensive UV exposure during the study (mountain sports, UV radiation, sunbathing, etc. . . . ).

This study was conducted as a multi-center, randomized, double-blind, controlled and parallel group trial. This superiority study involved Subjects of any race, aged 12 to 35 years inclusive with severe acne vulgaris and meeting specific inclusion/exclusion criteria.

A total of 440 Subjects were enrolled (220 in each group) in approximately 30 to 40 sites in USA and Canada. Approximately 12 Subjects were enrolled at each site.

Subjects were enrolled at Baseline and treated for 12 weeks with either Adapalene BPO Gel or its Vehicle Gel both associated with oral Doxycycline. There were two parallel groups, randomized in a ratio of 1:1.

There were 5 study visits: at Baseline, Week 2 (±2 days), Week 4 (±3 days), Week 8 (±3 days) and Week 12 (±5 days).

Each Subject did the followings:

Apply the topical study medication (Adapalene BPO Gel or its Vehicle Gel) once daily in the evening on the whole face, and Take the systemic study medication (Doxycycline) once daily in the morning with a meal.

The study period for the study was 12 weeks. It is generally agreed in acne clinical trials to evaluate the efficacy after 12 weeks of treatment. Eligible Subjects were evaluated five times (Baseline, Week 2, Week 4, Week 8 and Week 12—see table I: Study Flow Chart).

TABLE I

| PROCEDURES | Baseline | Week 2 (±2 days) | Week 4 (±3 days) | Week 8 (±3 days) | Week 12 (±5 days) | Final[a] procedures |
|---|---|---|---|---|---|---|
| Demographics/Medical History | X | | | | | |
| Concomitant Therapy | X | X | X | X | X | |
| Study Treatments Dispensed | X | | X | X | | |
| Lesion counts[b] | X | X | X | X | X | |
| Investigator Global Assessment | X | X | X | X | X | |
| Global Improvement | | | | | | X |
| Local Tolerability[c] | X | X | X | X | X | |
| PIH assessment[d] | X | X | X | X | X | |
| Adverse Events[e] | X | X | X | X | X | |
| Subject's Satisfaction Questionnaire | | | | | | X |
| Acne-QoL[f] | X | | | | | X |
| Qualification for the maintenance phase | | | | | | X[j] |

[a]To be performed at week 12 or before if early termination (including condition "clear").
[b]Inflammatory lesion counts, non-Inflammatory lesions and nodules/cysts counts.
[c]The Investigator must record and grade the severity of the signs and record the assessment of symptoms of local tolerability (erythema, dryness, scaling, and stinging/burning) at each visit.
[d]Postinflammatory Hyperpigmentation assessment only for Subjects with skin phototypes IV to VI.
[e]Adverse event onsets after subject signature of the informed consent form should be recorded on the AE Form of the CRF.
[f]Only for Subjects aged 13 years or older at Baseline; Subjects speaking French Canadian were not required to complete the questionnaire because there is no validated version in this language.

Study Design

Because Adapalene BPO Gel fixed combination was registered in USA and Canada before the study starts, this comparative study is considered as a Phase 3b. Doxycycline was prescribed in the USA and Canada as adjunctive treatment in acne vulgaris.

Subject selection and dosage for Doxycycline were based on the USA/Canada approved labeling of Doxycycline.

The dosage of Adapalene BPO was based on the Development Program (Phase 1 to 3 studies) currently under review by the Food and Drug Administration.

In this study, Adapalene BPO Gel and Doxycycline were used in association because they act on different pathophysiologic factors of acne vulgaris. Therefore, the associated use resulted in superior efficacy as compared to Doxycycline alone.

Subjects with mild and moderate acne are usually treated with topical treatments alone. For this reason, only Subjects with severe facial acne vulgaris were enrolled in this study. Severe acne corresponds to the clinical severity usually treated with combination therapies involving oral and topical agents.

Study Visit Description and Procedures 1.1 Baseline Visit

1. Review and explain the nature and the constraints of the study to the Subject and to parent or guardian if Subject under age of majority;
2. Have the Subject (and parent/guardian for Subject under age of majority) read, date and sign an IRB approved Informed Consent form(s). Give a dated and signed copy to each Subject and parent/guardian if applicable;
3. Assign a Subject identification number pre-printed on the case report form;
4. Question the Subject about demography, medical history, previous and concomitant therapies. Inform Subject about authorized and prohibited concomitant therapies. If the Subject requires a medication washout period, the Subject's Baseline evaluation must be conducted after the washout period is completed;
5. Evaluate the Subject according to inclusion and exclusion criteria (see sections 3.3 and 3.4);
6. If applicable, conduct a urine pregnancy test (UPT) for female Subjects of childbearing potential;
7. Conduct the Investigator Global Assessment of the face (IGA)—static disease assessment;

8. Conduct the initial facial inflammatory and non-inflammatory lesion counts (see Attachment 2);
9. Grade and record the severity of the signs and symptoms related to tolerability (erythema, dryness, scaling, and stinging/burning);
10. Grade and record severity of Postinflammatory Hyperpigmentation (PIH) for Subjects with skin phototypes IV to VI (according to T. B. Fitzpatrick's definitions);
11. Have the Subject complete the Acne-QoL questionnaire (only for Subjects aged 13 years old or older and English or Spanish native language—see Attachments 4);
12. For selected sites only (and only if Subject and parent/guardian if applicable accept through IRB approved information and consent form) take photographs of the face according to specific photographic procedures (see Section 6.3.2 and Attachment 5);
13. Question Subject and record occurrence of any Adverse Events;
14. The person in charge of study medication (quoted bellow the Study Drug Dispenser) will dispense the Baseline Visit kit in sequential order associated with the Subject's diary. Each Visit kit will contain two tubes of the topical investigational product. The Study Drug Dispenser will affix the tear-off label from the Visit kit containing investigational product tubes on the Drug Dispensation Log;
15. The Study Drug Dispenser will dispense also one Doxycycline box containing 100 tablets. The Study Drug Dispenser will record the Visit kit number on the Doxycycline box label and confirm Doxycycline dispensation on the Drug Dispensation Log;
16. Cetaphil® Gentle Skin Cleanser, Cetaphil® Moisturizing Lotion, Cetaphil® Daily Facial Moisturizer SPF 15 (non investigational product) will be dispensed also;
17. The Study Drug Dispenser—not involved in study efficacy and safety measurement criteria—will provide verbal and written instructions (see Attachment 1) about investigational and non-investigational products on how to use them, how to keep a record of missed doses and emphasize the importance of complying with the prescribed routine using the investigational products.
18. Schedule Week 2 (±2 days) post-Baseline visit.
1.2 Follow-Up Visits Week 2, 4 and Week 8
1. Question the Subject about the occurrence of any new adverse events and about any changes on adverse events ongoing at the last study visit. Document all changes on the Case Report Form;
2. Inquire as to whether concomitant therapies have been added, stopped, or changed since the Subject's last visit. Document all changes on the Case Report Form;
3. Conduct facial inflammatory and non-inflammatory lesion counts (see Attachment 2);
4. Conduct the Investigator Global Assessment of the face (IGA)—static disease assessment;
5. Grade and record the severity of the signs and symptoms related to tolerability (erythema, dryness, scaling, and stinging/burning);
6. Grade and record severity of PIH—for Subjects with skin phototypes IV to VI (according to T. B. Fitzpatrick's definitions);
7. At Weeks 4 and 8, conduct a UPT on Subjects of childbearing potential who has not had a menstrual period in the preceding four weeks;
8. At Weeks 4 and 8, for selected sites only, take photographs of the face according to the standard photographic procedure (see Attachment 5);
9. At Week 2, the Study Drug Dispenser checks the Subject's Treatment Diary and gives again Subject verbal and written instructions (see Attachment 1) on how to use investigational and non-investigational products, how to keep a record of missed doses and on how compliance to the routine with the investigational products is important;
10. At Weeks 4 and 8, the Study Drug Dispenser records investigational and non-investigational products compliance according to Subject's Treatment Diary and Subject's interview, collect the previous used Visit kit and dispense new Visit kit containing 2 tubes and affix the tear off label on Drug Dispensation Log and gives again Subject verbal and written instructions (see Attachment 1) on how to use investigational and non-investigational products, how to keep a record of missed doses and emphasize the compliance to investigational products;
11. Schedule next follow up visit [Week 4 (±3 days), Week 8 (±3 days) or Week 12 (±5 days)];
12. In case of any premature Termination of the study whatever the reason is, all checked study procedures of the corresponding visit should be conducted and recorded on the appropriate visit pages of the CRF. Then, the Final Procedures will have to be performed (Global Improvement, Satisfaction and Acne-QoL questionnaires) and the Exit Form should be completed by mentioning the principal reason for study discontinuation and conducting a pregnancy test on all Subjects of childbearing potential;
13. Furthermore, if premature termination reason is condition Clear (Subject graded as Clear at Week 2, 4 or 8), Subject will be invited to participate to the maintenance study (RD.03.5PR.29075). Investigator will have to record the entry or not in maintenance phase onto the CRF.
1.3 Week 12
1. Question the Subject about the occurrence of any new adverse events and about any changes on adverse events ongoing at the last study visit. Document all changes on the Case Report Form;
2. Inquire as to whether concomitant therapies have been added, stopped, or changed since the Subject's last visit. Document all changes on the Case Report Form;
3. Conduct the final facial inflammatory and non-inflammatory lesion counts (see Attachment 2);
4. Conduct the final Investigator Global Assessment of the face (IGA)—static disease assessment;
5. Grade and record the final severity of the signs and symptoms related to tolerability (erythema, dryness, scaling, and stinging/burning);
6. Grade and record the final severity of PIH—for Subjects with skin phototype IV to VI (according to T. B. Fitzpatrick's definitions);
7. For selected sites only, take photographs of the face according to the standard photographic procedure (see Attachment 5);
8. Records investigational and non-investigational products compliance according to Subject's Treatment Diary and Subject's interview;
9. Ensure that Subject has returned to the Study Drug Dispenser all used/unused investigational product tubes for weighing* and remaining investigational product tablets for counting*. All missing tubes/tablets must be explained by the Study Drug Dispenser on the Drug Dispensation Log comments section and on others accountability form or similar.
* Final weighing and counting were performed by the Sponsor at the end of the study.
1.4 Final Procedure
1. Grade and record the Global Improvement from Baseline to Last study visit—dynamic disease assessment;
2. Ask the Subject to complete the last Acne-QoL Questionnaire and Satisfaction Questionnaire and review the questionnaires for completion;

Test Materials
  Product Identification and Use
  1.1.2 Product Identity

|  | Galderma Product | Comparator Product | Associated Product |
|---|---|---|---|
| Trade Name | NA | NA | Doxycycline Hyclate |
| Name of Active Ingredient | Adapalene/Benzoyl Peroxide | NA | Doxycycline |
| Form | Gel | Gel | Tablet |
| Dose or Concentration | 0.1%/2.5% | NA | 100 mg |
| Manufacturer | Galderma Production | Laboratoires Galderma | Mutual Pharmaceutical Co., Inc (generic) NDC-0904-0430-61 |
| Packaging (primary) | Laminate tube 30 g | Laminate tube 30 g | 100 tablets in blister |
| Storage Requirements | Store at or below 25° C. (77° F.). Do not refrigerate | Store at or below 25° C. (77° F.). Do not refrigerate | Store between 15°-30° C. (59°-86° F.). Do not refrigerate |

1.1.3 Method of Treatment Assignment

Prior to the start of the study, a randomization list was generated by the Phase IV statistician from Galderma and transmitted to the assigned clinical packaging organization for labeling.

The RANUNI routine of the SAS systems was used for the kit number generation.

Kit numbers indicated on the randomization list corresponds to the kit number indicated on labels of the topical investigational products. This kit number was mentioned by the Study Drug Dispenser on the Doxycycline box label.

Topical treatments were balanced into 4 Subject consecutive blocks in 1:1 ratio for each group. Complete blocks of treatment materials were sent to the investigational sites, such that each Investigator enrolled approximately 12 Subjects.

The randomization list and the electronic file was secured in a locked cabinet and in an electronic file with restricted access to only the designated personnel directly responsible for labeling and handling the study medications until the study database was locked and ready to be unblinded.

For treatment allocation, each Subject who fulfiled all criteria to receive the study treatments at the Baseline visit, was dispensed a Visit box from the Subject kit allocated in the chronological order of his/her inclusion in the study, and no number was omitted or skipped.

The designated study personnel in charge of the study medications (quoted below Study Drug Dispenser) gave each Subject verbal instructions on "how to use" the investigational and non-investigational products. Subject kist (Adapalene BPO Gel tubes or its Vehicle Gel tubes) were dispensed according to the chronological order of enrollment of subjects into the study along with one Doxycycline box.

Subjects treated the entire face once daily in the evening with either Adapalene BPO Gel or its Vehicle Gel for 12 weeks (see Attachment 1) along with taking 1 Doxycycline tablets in the morning with food.

The Study Drug Dispenser was different from the study efficacy and safety Evaluator in order to keep the blind (see section 5.4).

The treatment administration is further described below.

|  | Adapalene BPO Gel | Vehicle Gel | Doxycycline tablet |
|---|---|---|---|
| Concentration | 0.1%/2.5% | NA | 100 mg |
| Dose Regimen | Once daily in the evening | Once daily in the evening | One tablet in the morning |

-continued

|  | Adapalene BPO Gel | Vehicle Gel | Doxycycline tablet |
|---|---|---|---|
| Period of Administration | 12 weeks | 12 weeks | 12 weeks |
| Route of Administration | Topically to the entire face | Topically to the entire face | Oral with food |

Efficacy and Safety Assessment

Clinical evaluations were performed by the same Evaluator (Investigator or designee) throughout the study.

If it was not possible to use the same Evaluator to follow the Subject, then evaluations overlapped for at least one visit in order to examine the subject together and discuss findings.

1. Efficacy Assessment
1.1 Efficacy Criteria

The primary efficacy criterion was:

Percent change from baseline in total lesion count (sum of non inflammatory and inflammatory lesions) at Week 12.

The secondary efficacy criteria was:

Percent change from baseline in total lesion was counted at each intermediate visit;

Percent change from baseline in Inflammatory lesion was counted at each post baseline visit;

Percent change from baseline in Non-inflammatory lesion was counted at each post baseline visit;

The changes in Investigator Global Assessment at each post Baseline visit was compared to Baseline;

Global Improvement from Baseline at Week 12/early termination.

1.2 Efficacy Measurements

Lesion Counts

Each type of lesion will be counted separately and recorded on the appropriate Case Report Form. The Evaluator (Investigator or designee) will take the lesion counts from left and right forehead, left and right cheeks, and chin above the jaw line (excluding the nose).

The lesion counts will be electronically added together to obtain a total lesion count.

The following are the definitions of the lesions that will be counted.

Non-Inflammatory Lesions

Open Comedone—A mass of sebaceous material that is impacted behind an open follicular orifice (blackhead).

Closed Comedone—A mass of sebaceous material that is impacted behind a closed follicular orifice (white head).

Inflammatory Lesions

Papules—A small, solid elevation less than one centimeter in diameter. Most of the lesion is above the surface of the skin.

Pustules—A small, circumscribed elevation of the skin which contains yellow-white exudates.

Nodules/Cysts—A circumscribed, elevated, lesion generally more than 1.0 cm in diameter (No more than 2 nodules/cysts will be allowed for study participation).

Investigator's Global Assessment

The Evaluator (Investigator or designee) assessed the severity (global grade) of acne at Baseline and at each post-baseline visit. The global severity assessment was used to define the acne severity. The Evaluator evaluated the Subject's acne at each visit performing a static ("snapshot") evaluation of acne severity.

The Evaluator maked no reference to Baseline or other previous visits when evaluating the Subject's facial acne.

The global severity assessment is outlined in the following table:

| | Investigator's Global Assessment | |
|---|---|---|
| 0 | Clear | Residual hyperpigmentation and erythema may be present |
| 1 | Almost Clear | A few scattered comedones and a few small papules. |
| 2 | Mild | Some comedones and some papules and pustules. No nodules present |
| 3 | Moderate | Many comedones, papules and pustules. One nodule may be present |
| 4 | Severe | Covered with comedones, numerous papules and pustules and few nodules and cysts may be present |
| 5 | Very severe | Highly inflammatory acne covering the face; with nodules and cysts present |

If Subject is graded as clear at Week 2, 4 or 8, the Subject had to stop the study at this point and corresponding Study Visit and the Exit Form were completed. Furthermore, Subject was invited to participate to the maintenance study (RD.03.5PR.29075).

Global Assessment of Improvement

The Evaluator (Investigator or designee) conducted a Global Assessment of Improvement by comparing Week 12 (or Early Termination) facial skin condition to skin condition at Baseline. Subjects were evaluated according to the following scale:

| | Global Assessment of Improvement from Baseline | |
|---|---|---|
| 0 | Complete improvement | All signs and symptoms of disease have resolved (100% improvement from Baseline) |
| 1 | Excellent improvement | Nearly all signs and symptoms cleared (90% improvement from Baseline). Only minimal residual signs and symptoms remain |
| 2 | Marked Improvement | Majority of the signs and symptoms have resolved (about 75% improvement from Baseline) |
| 3 | Moderate Improvement | Significant improvement, but many signs and symptoms remain (about 50% improvement from Baseline) |
| 4 | Minimal Improvement | Slight overall improvement, but not clinically significant (about 25% improvement from Baseline) |
| 5 | No Change | Overall severity similar from Baseline |
| 6 | Worse | Worse than Baseline |

2) Safety Assessment 2.1 Tolerability Assessment:

Erythema, scaling, dryness, and stinging/burning were graded at each visit as follows:

| Erythema - abnormal redness of the skin. | | |
|---|---|---|
| None | 0 | No erythema |
| Mild | 1 | Slight pinkness present |
| Moderate | 2 | Definite redness, easily recognized |
| Severe | 3 | Intense redness |
| Scaling - abnormal shedding of the stratum corneum. | | |
| None | 0 | No scaling |
| Mild | 1 | Barely perceptible shedding, noticeable only on light scratching or rubbing |
| Moderate | 2 | Obvious but not profuse shedding |
| Severe | 3 | Heavy scale production |
| Dryness - brittle and/or tight sensation. | | |
| None | 0 | No dryness |
| Mild | 1 | Slight but definite roughness |
| Moderate | 2 | Moderate roughness |
| Severe | 3 | Marked roughness |
| Stinging/Burning - prickling pain sensation immediately after (within 5 minutes) dosing. | | |
| None | 0 | No stinging/burning |
| Mild | 1 | Slight warm, tingling/stinging sensation; not really bothersome |
| Moderate | 2 | Definite warm, tingling/stinging sensation that is somewhat bothersome |
| Severe | 3 | Hot, tingling/stinging sensation that has caused definite discomfort |

Erythema, scaling, and dryness were be evaluated by the Evaluator (Investigator or designee). Stinging and burning were recorded by the Evaluator after discussion with the subject.

2.2 Adverse Events (AEs):

Adverse Events were recorded during each follow up visit. All clinical medical events, whether observed by the Investigator or reported by the Subject and whether or not thought to be product- or study procedure-related were considered adverse events and recorded on the appropriate Adverse Event form except those events assessed/reported as Tolerability Assessments (see section 7.1.1.).

3) Others 3.1 Subject's Satisfaction Questionnaire:

At Week 12/Early Termination, Subjects completed a Satisfaction Questionnaire regarding the treatments they have been using in this study.

3.2 Acne-Specific Quality of Life Questionnaire (Acne-QoL):

It was collected at Baseline and Week 12/Early Termination. The Investigator or designee provided the subject (only subjects aged 13 and older) with the Acne-QoL Form and instruct the subject to read and answer all 19 quality of life questions. The questionnaire measured the impact of facial acne on health-related quality of life. Subjects speaking French Canadian were not required to complete such questionnaire because no validated translation exists.

The 19 questions are on a 0-6 scale and divided into 4 domains: Self-perception (5 questions—total score range from 0 to 30), Role-emotional (5 questions—total score range from 0 to 30), Role-social (4 questions—total score range from 0 to 24) and acne symptoms (5 questions—total score range from 0 to 30).

If a Subject turns to 13 years old at Week 12/Early Termination study visit and if Subject is entering in the maintenance study (RD.03.5PR.29075), he/she had to complete Acne-QoL questionnaire.

The Investigator or designee had to check the questionnaires prior to the Subject leaving the site in order to verify that all questions were answered.

3.3 Visible and UV Light Photographs

Subjects were photographed at Baseline, Week 4, Week 8 and Week 12/Early termination.

Visible and UV fluorescence light photos with specific digital cameras were conducted at selected sites familiar with this technique.

The imaging of porphyrin fluorescence is a valuable tool to demonstrate the presence of P. acnes.

Metabolites of P. acnes (porphyrins) have an orange red fluorescence. It has been demonstrated in previous studies that the intensity of orange fluorescence correlates with the presence and activity of P. acnes. A reduction in the number of orange fluorescent follicles during therapy was interpreted as a measure of efficacy of investigational products on P. acnes activity.

Both assessments were performed according to a specific procedure described in Attachment 5.

Appropriateness of Measurements

Efficacy was the main evaluation criterion and was evaluated by lesion counting, which is a current practice to assess severity of acne.

An Investigator Global Assessment was also performed. This evaluation scale is non invasive technique currently used to assess acne severity.

The Global Assessment of Improvement from baseline is also an evaluation scale commonly used in clinical studies for dermatological products.

The same Evaluator (Investigator or designee) evaluated the same Subject at each visit throughout the study.

Adverse Events

Throughout the course of the study, all adverse events were monitored and reported on an Adverse Event Form disclosing any requested and known information. When adverse events occur, the main concern was the safety of the study Subjects.

Definitions

Adverse Events (AE)

An adverse event (AE) can be any unfavorable and/or unintended sign (including an abnormal laboratory finding), symptom, or disease temporally associated with the use of a medicinal/investigational product, whether or not related to the medicinal/investigational products or to the study procedures.

Thus any new sign, symptom or disease, or clinically significant increase in the intensity of an existing sign, symptom or disease, were considered as an adverse event.

Notes:

Clinically significant worsening of the disease/condition being evaluated, which occurs during the study, was considered an adverse event, Any new sign or symptoms suffered by the Subject which appeared after accidental or intentional overdose or misuse were also reported as an adverse event.

Any adverse event, whether or not it is related to the investigational products or to the study procedures, was reported on the Adverse Event form along with the diagnosis preferably or signs/symptoms description, the date of onset, the severity, the seriousness, the relationship and the action taken with the investigational product but also the treatment given to treat the AE and the final AE outcome.

Assessment of AE seriousness, severity and causality was based on specific definitions.

If the Subject discontinued due to an Adverse Event, the Adverse Event and Exit Forms had to be completed.

Side effects may be expected during topical study treatment, the characteristics of which are described in this protocol (e.g., erythema, scaling, dryness, and stinging/burning). The course of these expected events was assessed and reported on the tolerability assessments. An Adverse Event Form was completed only if the severity of the expected signs and symptoms was such that an interruption of the Subject's participation in the study occurred at Investigator's decision and/or if a concomitant medication (except provided moisturizers) was prescribed to treat the sign/symptom.

Serious Adverse Events (SAE)

A Serious Adverse Event is any untoward medical occurrence that at any dose:

results in death, is life-threatening, requires inpatient hospitalization or prolongation of existing hospitalization, results in persistent or significant disability/incapacity, or is a congenital anomaly/birth defect.

And also:

Other important medical events that jeopardize the Subject or require intervention to prevent one of the outcomes listed above.

Note:

The term "life-threatening" refers to an event in which the Subject was at risk of death at the time of event; it does not refer to an event which hypothetically might have caused death if it was more severe.

Hospitalization solely for the purpose of diagnostic tests, even if related to an adverse event, elective hospitalization for an intervention which was already planned before the inclusion of the Subject in the study, and admission to a day-care facility may not themselves constitute sufficient grounds to be considered as a serious adverse event.

Severity

Severity is a clinical determination of the intensity of an adverse event.

The severity assessment for an adverse event was completed using the following definitions as a guideline for all adverse events occurring during this study (usually used in all clinical trials conducted/sponsored by Galderma):

| | |
|---|---|
| Mild: | Awareness of sign or symptom, but easily tolerated |
| Moderate: | Discomfort, enough to cause interference with usual activity |
| Severe: | Incapacitating with inability to work or perform usual activity |

Relationship to Study Drugs

The relationship assessment for an adverse event was completed using the following definitions as a guideline for all adverse events occurring during clinical trials conducted or sponsored by Galderma:

| | |
|---|---|
| Definitely unrelated: | Should be reserved for those events which occur prior to investigational product(s) administration (e.g., washout or single-blind placebo) or for those events which cannot be even remotely related to study participation (e.g., injuries sustained as a passenger in an automobile accident). |

| | |
|---|---|
| Unlikely: | There is no reasonable temporal association between the investigational product(s) and the event and the event could have been produced by the Subject's clinical state or other modes of therapy administered to the Subject. |
| Possible: | The event may or may not follow a reasonable temporal sequence from investigational product(s) administration but seems to be the type of reaction that cannot be dismissed as unlikely. The event could have been produced or mimicked by the Subject's clinical state or by other modes of therapy concomitantly administered to the Subject. |
| Probable: | The event follows a reasonable temporal sequence from investigational product(s) administration, abates upon discontinuation of the investigation product, and cannot be reasonably explained by the known characteristics of the Subject's clinical state. |
| Definitely related: | Should be reserved for those events which have no uncertainty in their relationship to investigational product(s) administration: this means that a re-challenge was positive. |

For AEs graded possible, probable or definitely related; the Investigator determined whether is related to topical or oral investigational product or both.

Suspected Sensitization (Patch Test)

In order to confirm sensitization, additional patch-tests can be conducted; a first patch-test using the investigational Gel products and a second one—only if positive response to the first patch-test—using all separate components of the investigational Gels.

At least two weeks after discontinuation of the investigational Gel product applications, patches were applied for 48 hours on the Subject's arm or back.

Readings were performed between 15 to 30 minutes and then 48 hours after the patches removal.

The patch-tests were supplied by Galderma and the results from each patch test will be reported as directed by the Sponsor.

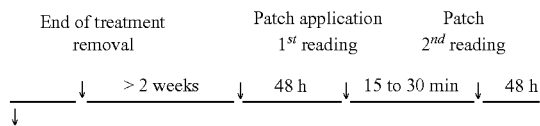

Procedures for Reporting Adverse Events

At each visit, the Investigator questioned the Subject about adverse events using an open question taking care not to influence the Subject's answer (e.g. "Have you noticed any change in your health since the last visit?"). Directed questioning and examination was then done when appropriate.

All reported adverse events were documented on the appropriate Case Report Form without omitting any requested and known information.

Every time a concomitant therapy was reported during the study, an Adverse Event Form was completed if appropriate and the reason for the treatment noted.

If an adverse event persisted at the end of the study, the Investigator ensured a follow-up of the Subject until the Investigator and Galderma agreed the event was satisfactorily resolved.

Statistical Methods
Statistical and Analytical Methods

The main purpose of this study was to demonstrate the superiority of Adapalene BPO Gel associated with Doxycycline compared to antibiotic alone in terms of efficacy i.e. percent change in total lesion counts of acne vulgaris.

Variables to be Statistically Analyzed

The following variables will be analyzed:
Primary Efficacy Variable:
Percent change from Baseline in total lesion count (sum of non inflammatory and inflammatory lesions) at Week 12.

Secondary Efficacy Variables:
Percent change from Baseline in total lesion count at each intermediate visit
Percent change from Baseline in inflammatory lesion count at each post Baseline visit
Percent change from Baseline in non-inflammatory lesion count at each post Baseline visit
Investigator Global Assessment at each post Baseline visit: % of Subjects across scores
Global Improvement from Baseline at week 12/early termination: % of Subjects across scores
Safety Variables:
Local tolerance worst-score post Baseline: % of Subjects across scores
Postinflammatory Hyperpigmentation worst-score post Baseline: % of Subjects across scores
Others:
Subject's questionnaires (satisfaction questionnaire and Acne-QoL)

Populations Analysed, Evaluability and Limitation Evaluation of Bias

The following populations will be analyzed:
The Per-Protocol Efficacy Population (PP)

This population consisted of all enrolled and randomized Subjects, except Subjects considered not evaluable due to major deviations from the protocol.

Major deviations were defined after data entry and before unblinding the study treatment, and may include: inclusion criteria not respected, non available efficacy assessment, interfering therapy at inclusion, etc.

The Intent-to-Treat Efficacy Population (ITT)

This population consisted of the entire population enrolled and randomized (i.e., assigned a treatment (or kit) number.

The Safety Population (APT)

This population consisted of the intent-to-treat population, after exclusion of Subjects who never took the treatment with certainty based on monitoring report.

Missing Values

For efficacy variables, in order to evaluate the effect of major deviations or of data exclusions, the ITT population were analyzed at each visit using the last observation carried forward (LOCF) to impute missing values. If no post-baseline data was available, baseline was carried forward. Thus, the number of Subjects did not vary at each visit. The other missing values were not replaced (observed data).

Data Presentation and Graphics

All continuous data were summarized using usual statistics: number of values, mean, median, standard deviation, minimum and maximum, and by frequency distribution (n, %) for qualitative data. For ordinal data, both frequency distribution and usual statistics were presented. All tables were presented by study medication and by visit.

For the safety variables, all summaries were based on the safety population (APT). The adverse events were descriptively summarized (n, %) by relationship to investigational products and by intensity (i.e. mild, moderate and severe). In the case of an adverse event occurring more than once during the study period, the adverse event with the highest drug related rating in that period was used in the summary by categories of relationship to drug. Similarly, the adverse event with the highest intensity in that period was used in the summary by intensity. The adverse experiences were summarized (n, %) within SOC and preferred term (MedDRA). Deaths and serious adverse events were reported as well as withdrawals due to adverse events.

Statistical Analyses

The definition of the populations was finalized after a blind data review meeting, during which the distribution of Subjects per site were reviewed. In case of too small sites or in case of severe unbalance between the size of sites, some sites were combined, e.g. per geographical area, to form analysis-center for purpose of stratification of the statistical analyses.

The primary objective of this study was to demonstrate a superiority of Adapalene BPO Gel associated with Doxycycline compared to its Vehicle Gel associated with Doxycycline, in terms of percent change in total lesion counts at Week 12 (LOCF).

This objective was shown by using the Cochran-Mantel-Haenszel (CMH) statistic, stratified by center (or analysis-center) after ridit transformation with the row mean difference statistics, testing the hypothesis of equality. The p-value was inferior to 0.05 at Week 12, on ITT/LOCF population. PP analysis was also performed to assess the robustness of the results obtained on ITT/LOCF population.

The secondary efficacy variables, local tolerance worst-score, PIH worst-score and questionnaires were analyzed similarly as primary analysis on appropriate population.

Each test was two-sided, at the 0.050 significance level.

The Subject disposition, previous and concomitant medication, study treatments duration/compliance, adverse event(s), demographics, baseline characteristics, safety variables (except the worst-scores), inflammatory, non-inflammatory and total lesion counts were descriptively summarized on appropriate population.

Example 2

Clinical Test of Treatment of Severe Acne Vulgaris with a Gel Composition Containing Adapalene 0.1%/Benzoyl Peroxide 2.5% Gel Associated with Doxycycline Hyclate 100 mg Tablets The clinical study protocols were described in Example 1. All the treatments were administered once a day for 12 weeks, to 517 patients suffering from acne.

1. Epiduo Gel

Epiduo gel containing Adapalene 0.1%/Benzoyl Peroxide 2.5% Gel was used for the study. Each subject applied Epiduo gel once daily in the evening.

Epiduo gel has the following formulation (expressed as % weight/total weight).

| | |
|---|---|
| Adapalene | 0.10% |
| Benzoyl peroxide | 2.50% |
| Copolymer of acrylamide & sodium acryloyl-dimethyltaurate | 4.00% |
| Sodium docusate | 0.05% |
| Disodium EDTA | 0.10% |
| Glycerol | 4.00% |
| Poloxamer 124 | 0.20% |
| Propylene glycol | 4.00% |
| Purified water | qs 100% |

2. Doxycycline Hyclate

Doxycycline Hyclate 100 mg tablets were used for the study. Subject selection and dosage for Doxycycline were based on the USA/Canada approved labeling of Doxycycline. Each subject toke Doxycycline once daily in the morning with a meal.

3. Vehicle Gel

The result with the vehicle gel, which is essentially the same formulation of Epiduo Gel without Adapalene and benzoyl peroxide was used as baseline for the study.

4. Results:

The results of the current study were compared with the results of Epiduo study that was previously conducted under the same study protocols, which was described in WO2008/006888, and incorporated by its entirety herein.

The comparative results are presented in the Table 1.

TABLE 1

Comparison of efficacy results in 12 weeks

| Median changes (%) | Epiduo Gel ® + Doxycycline | Epiduo Gel ® | Doxycycline + Vehicle gel | Vehicle gel |
|---|---|---|---|---|
| Total lesions | −64.0 | −51.0 | −41.0 | −31.0 |
| Inflammatory lesions | −72.0 | −17.0 | −48.0 | −11.0 |
| Non inflammatory lesions | −61 | −51.2 | −40.0 | −37.5 |
| Success rate | 31.5 | 27.5 | 8.4 | 9.9 |

1) For the four main criteria of the study: degree of success and reduction as a percentage of the three types of lesion, the fixed combination plus Doxycycline was found to be statistically superior to the fixed combination (the Epiduo Gel) or Doxycycline alone.

2) When the effect of the gel used as vehicle is subtracted from the effect of the fixed combination plus Doxycycline, the fixed combination (the Epiduo Gel), and Doxycycline alone, the net clinical benefit of the therapy regimen of this invention is significantly superior to the sum of the net clinical benefits of fixed combination (the Epiduo Gel), and Doxycycline alone.

Thus, these results show a synergistic effect of the therapy regimen of this invention in all four categories, i.e., degree of success and progress as a percentage of the three types of lesion.

In addition, with comparing Epiduo® gel+doxycycline Vehicle Gel+Doxycycline at all study visits, these results also show:

a) As showed in FIG. 1, for total lesions results, Epiduo® Gel+Doxycycline is significantly superior to Vehicle Gel+Doxycycline at all study visits and as early as Week 2 (−21% versus −13%). At Week 12, a 64% decrease is observed for Epiduo® Gel+Doxycycline versus −41%. The PP population confirms the significant superiority of Epiduo® Gel+Doxycycline compared to Vehicle Gel+Doxycycline with a reduction of the total lesions of −66% versus −43% at week 12.

b) As showed in FIG. 2, the percent reduction in inflammatory lesions shows a rapid onset of action statistically significant from week 2 (−27% versus −22%) to week 12 (−72% versus −48%) in favor of Epiduo® Gel+Doxycycline compared to Vehicle Gel+Doxycycline.

c) As showed in FIG. 3, the percent reduction in non-inflammatory lesions shows a rapid onset of action statistically significant from week 2 (−17% versus −10%) to week 12 (−61% versus −40%) in favor of Epiduo® Gel+Doxycycline compared to Vehicle Gel+Doxycycline.

d) As showed in FIG. 4, in term of success rate (clear+almost clear), a significant difference was observed from week 8 (9.9% vs. 2.6%) to week 12 (31.5% vs. 8.4%) in favor of Epiduo® Gel+Doxycycline compared to Vehicle Gel+Doxycycline, with a sharp increase during the last month for Epiduo® Gel+Doxycycline.

What is claimed is:

1. A concurrent therapy regime/regimen for inhibiting or treating an acne related disease, comprising:
   (a) topically applying onto the skin of an individual subject in need of such treatment, a therapeutically effective amount of a fixed-dose combination which comprises a retinoid which is adapalene and a topical antibacterial agent which is benzoyl peroxide, in the same vehicle, for a first predetermined period of time of 12 weeks; concurrently (b) orally administering to said individual subject a therapeutically effective amount of an oral antibiotic which is doxycycline hyclate with the fixed-dose combination for said first predetermined period of time of 12 weeks; and (c) optionally continuing the fixed-dose combination for another period of time as needed;
   wherein said concurrent steps (a) and (b) provide a synergistic effect; and
   wherein said synergistic effect is superior in terms of a resulting reduction in total lesions, reduction in inflammatory lesions, and reduction in non-inflammatory lesions when compared to a regime/regimen for inhibiting or treating an acne related disease with said fixed-dose combination or said oral antibiotic alone after 12 weeks of treatment.

2. The regime/regimen as defined by claim 1, wherein the acne related disease is acne vulgaris.

3. The regime/regimen as defined by claim 2, wherein the acne vulgaris is moderate to severe acne vulgaris.

4. The regime/regimen as defined by claim 1, wherein the fixed-dose combination is administered once a day.

5. The regime/regimen as defined by claim 1, wherein the fixed-dose combination is topically applied in the evening and the oral antibiotic product is administered in the morning.

6. The regime/regimen as defined by claim 1, wherein the fixed-dose combination comprises adapalene and benzoyl peroxide in a gel form.

7. The regime/regimen as defined by claim 6, wherein the gel form is an aqueous gel form.

* * * * *